(12) United States Patent
Windmueller et al.

(10) Patent No.: US 6,515,096 B2
(45) Date of Patent: Feb. 4, 2003

(54) STABLE 1:1 MONOADDUCTS OF SECONDARY AMINOALKYLALKOXYSILANES AND DIISOCYANATES AND A PROCESS FOR PREPARING THEM

(75) Inventors: Manuela Windmueller, Marl (DE); Stephan Kohlstruk, Marl (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/777,857

(22) Filed: Feb. 7, 2001

(65) Prior Publication Data

US 2001/0031848 A1 Oct. 18, 2001

(30) Foreign Application Priority Data

Mar. 18, 2000 (DE) .......................... 100 13 628

(51) Int. Cl.$^7$ .................. C08G 77/26; C07F 7/10
(52) U.S. Cl. .................. 528/38; 528/26; 528/25; 556/413; 556/414
(58) Field of Search ............... 528/38, 26, 25; 556/413, 414

(56) References Cited

U.S. PATENT DOCUMENTS

| | | | |
|---|---|---|---|
| 3,627,722 A | 12/1971 | Seiter | |
| 4,067,844 A | 1/1978 | Barron et al. | |
| 4,374,237 A | 2/1983 | Berger et al. | |
| 4,798,878 A | 1/1989 | Brinkmann et al. | |
| 6,046,270 A | * | 4/2000 | Roesler et al. |

FOREIGN PATENT DOCUMENTS

| | | |
|---|---|---|
| DE | 27 38 979 | 3/1979 |
| DE | 3 220 865 | 12/1983 |
| DE | 32 22 860 | 12/1983 |
| DE | 3 4 26 987 | 1/1986 |
| EP | 0 082 528 | 6/1983 |
| EP | 0 158 893 | 10/1985 |
| EP | 0 182 924 | 6/1986 |
| EP | 0 268 559 | 5/1988 |
| EP | 0 355 426 | 2/1990 |
| EP | 0 649 850 | 4/1995 |
| EP | 1 013 685 | 6/2002 |

OTHER PUBLICATIONS

V. W. Siefken, *Mono–und Polyisocyanata, Justus Liebigs Annalen Der Chemie*, 562, pp. 76–136 (148).

* cited by examiner

Primary Examiner—Robert Dawson
Assistant Examiner—Kuo-Liang Peng
(74) Attorney, Agent, or Firm—Oblon, Spivak, Mcclelland, Maier & Neustadt, P.C.

(57) ABSTRACT

Stable 1:1 monoadducts of secondary aminoalkylalkoxysilanes and diisocyanates, and a process for preparing them.

14 Claims, No Drawings

STABLE 1:1 MONOADDUCTS OF SECONDARY AMINOALKYLALKOXY-SILANES AND DIISOCYANATES AND A PROCESS FOR PREPARING THEM

BACKGROUND OF THE INVENTION

1. Field of the Invention

The present invention relates to stable 1:1 monoadducts of secondary aminoalkylalkoxysilanes and diisocyanates having a free diisocyanate content of less than 0.6% by weight and to a process for preparing the adducts. These monoadducts comprise difunctional monomers containing urea groups, a reactive isocyanate function, and crosslinkable silicon.

2. Discussion of the Background

The monoadducts of aminoalkylalkoxysilanes and diisocyanates belong to the class of the isocyanatoorganosilanes. A series of processes has been developed for preparing isocyanatoorganosilanes, these processes differing in terms, for example, their economics, efficiency, yield, and technical prerequisites (cf. EP 0 649 850). The process of the invention described herein is suitable both for preparing laboratory amounts and for industrial scale production.

Owing to their difunctionality, isocyanatoorganosilanes are synthesis building blocks of diverse usefulness which combine the high surface activity of the siloxanes with the high reactivity of the isocyanates and can be utilized to combine conventional polymer chemistry with silicone chemistry. The hydrolyzable silyl group is able to crosslink by way of a "silane polycondensation" in the presence of moisture, and the isocyanate groups as well are able to combine with one another under the effect of moisture. In addition to the reaction with hydroxy-functional coreactants, the isocyanate group offers the further option of the NCO/NH reaction. Both functionalities make it possible in principle to effect chemical attachment of the building block to customary polymer materials and thus a tailored modification of these materials The literature describes moisture-curing sealing compounds based on totally or partially silane-capped, isocyanate-terminated polyurethane prepolymers (EP 0 355 426, EP 0 082 528, DE 27 38 979, DE 34 26 987, EP 0 158 893, U.S. Pat. No. 4,374,237). Monoadducts of aminoalkylalkoxysilanes and diisocyanates have been used to prepare such systems. They also find application in the field of crosslinkable adhesives (DE 32 20865, DE 32 22 860). EP 0 182 924 describes the preparation and use of adhesion-promoting coatings of poly(meth)acrylates and isocyanate-functional alkoxysilanes, and EP 0 268 559 describes silicon-modified isophorone isocyanates as adhesion promoters. In principle, silicon-modified isocyanates containing urea groups are also suitable for such an application.

1:1 adducts of diisocyanates and aminoalkylalkoxy-silanes are not unknown (cf., e.g., DE 32 20 865). Their mode of preparation - reacting the two components in a molar ratio of approximately 1:1 - has the inevitable consequence, however, that they are obtained not in pure, isolated form but rather as a mixture containing relatively large amounts of bisadduct (diisocyanate-aminoalkylsilane 1:2) and unreacted diisocyanate. Unlike the 1:1 adduct, the former, as a disilane compound, is no longer a difunctional building block having chemical functions which are reactive independently of one another. It impairs the quality of the monoadduct and may also not be without deleterious effects on the quality and pattern of properties of the target end products. A high proportion of monomeric diisocyanate is intolerable from a toxicological standpoint. Isocyanates are highly reactive compounds, and many representatives of this class are classified as toxic. A high residual proportion of monomeric diisocyanate in the product must absolutely be avoided, since isocyanates are taken in predominantly by way of the respiratory tract and the vapor pressure of the monomer is much higher than in the case of the 1:1 adduct.

It is known that primary aminoalkylsilanes are unsuitable for the partial end capping of NCO prepolymers because the free isocyanate groups react further with the urea groups of the capped termini to form biurets. Gelling is the consequence in this reaction. According to U.S. Pat. No. 4,374,237, in contrast to the teaching of U.S. Pat. No. 3,627,722 and U.S. Pat. No. 4,067,844, the gelling problem cannot be solved even by using customary secondary aminoalkylsilanes instead of primary aminoalkylsilanes. A surprising exception specified is a group of particular secondary aminoalkylsilanes, including N,N-bis[(3-triethoxysilyl)propyl]amine as a suitable representative example.

Furthermore, experiments have shown not only that NCO-containing adducts of isocyanates and aminoalkylalkoxysilanes are hampered by the problem of gelling as a result of biuret formation but also that there is a marked instability with respect to cleavage back to the starting materials. This tendency for reversal of the formation reaction—the urea group breaks down with reformation of the isocyanate group and the amine—has been observed for primary and secondary aminoalkylsilanes, including N,N-bis[(3-triethoxysilyl)propyl]amine.

It would be advantageous and desirable if the target monoadducts (1:1) of aminoalkylalkoxysilanes and diisocyanates did not have the disadvantages described above.

SUMMARY OF THE INVENTION

It is an object of the present invention to provide gelling-stable and recleave-stable monoadducts (1:1) of aminoalkylalkoxysilanes and diisocyanates having a relatively low free diisocyanate content.

Surprisingly, the present invention demonstrates that it is possible to obtain low-monomer, stable monoadducts (1:1) of aminoalkylalkoxy-silanes and diisocyanates by reacting particular secondary aminoalkylalkoxysilanes with diisocyanates and subsequently conducting a monomer separation by short path distillation.

The invention provides stable 1:1 monoadducts of aminoalkylalkoxysilanes and diisocyanates having a free diisocyanate content of less than 0.6% by weight, where the adducts comprise secondary aminoalkylalkoxysilanes of the formula I:

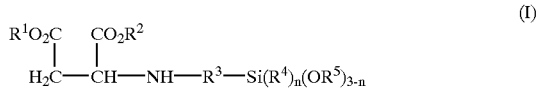

where
- $R^1$ and $R^2$ are identical or different $C_1$–$C_8$ alkyl groups;
- $R^3$ is a $C_1$–$C_5$ alkylene group;
- $R^4$ and $R^5$ are identical or different $C_1$–$C_{18}$ alkyl groups or alkoxyalkylene groups having up to 5 carbon atoms; and
- n is 0, 1 or 2; and diisocyanates.

Accordingly, the present invention provides a stable 1:1 monoadduct of (a) at least one aminoalkylalkoxysilane represented by formula I:

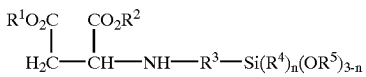
(I)

wherein
R¹ and R² are identical or different $C_1$–$C_8$ alkyl groups;
R³ is a $C_1$–$C_5$ alkylene group;
R⁴ and R⁵ are identical or different $C_1$–$C_8$ alkyl groups or alkoxyalkylene groups having up to 5 carbon atoms; and
n is 0, 1 or 2; and
(b) at least one diisocyanate,
wherein the monoadduct has a free diisocyanate content of less than 0.6% by weight.

The present invention also provides a process for preparing the stable 1:1 monoadduct, comprising:
reacting said aminoalkylalkoxysilane and said diisocyanate to produce said monoadduct, to produce said monoadduct, and then
removing unreacted diisocyanate such that the diisocyanate content of said monoadduct is less than 0.6% by weight.

The present invention additionally provides a process for preparing stable 1:1 monoadducts of aminoalkylalkoxysilanes and diisocyanates having a free diisocyanate content of less than 0.6% by weight, which comprises reacting 5–20 mol of diisocyanate with 1 mol of aminoalkylalkoxysilane, the diisocyanate being introduced initially at room temperature and the aminoalkylalkoxysilane being added dropwise to this initial charge at a rate such that the temperature increase does not exceed 100° C., and, after the end of the reaction, separating off the unreacted diisocyanate from the reaction product by means of a flash distillation at 80–160° C./0.04–0.2 mbar.

Various other objects, features and attendant advantages of the present invention will be more fully appreciated as the same becomes better understood from the following detailed description.

DETAILED DESCRIPTION OF THE PREFERRED EMBODIMENTS

Secondary aminoalkylalkoxysilanes of the invention are those represented by formula

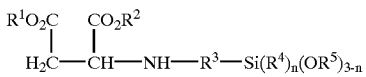
(I)

where
R¹ and R² are identical or different $C_1$–$C_8$ alkyl groups, preferably $C_1$–$C_4$ alkyl groups;
R³ is R $C_1$–$C_5$ alkylent group;
R⁴ and R⁵ are identical or different $C_1$–$C_{18}$ alkyl groups or alkoxyalkylene groups having up to 5 carbon atoms; and
n is 0, 1 or 2.

As described above R¹ and R² may have 1 to 8 carbon atoms, inclusive of all specific values and subranges therebetween such as 2, 3, 4, 5, 6 and 7 carbon atoms. R3 may have 1 to 5 carbon atoms, inclusive of all specific values and subranges therebetween such as 2, 3 and 4 carbon atoms. R⁴ and R⁵ may be a $C_1$–$C_{18}$ alkyl group. This range for the number of carbon atoms includes all specific values and subranges therebetween such as 2, 3, 4, 6, 8, 10, 12, 14, 16 and 18 carbon atoms. R⁴ and R⁵ may be an alkoxyalkylene group having up to 5 carbon atoms, i.e., may have 1, 2, 3, 4 or 5 carbon atoms.

Examples of suitable aminoalkylalkoxysilane compounds are described in EP 596 360, incorporated herein by reference. These aminoalkylalkoxysilanes are prepared by Michael addition of primary aminoalkoxysilanes represented by formula II:

(II)

with maleic and/or fumaric esters represented by formula III:

(III)

where the structural variables are as defined above.

Examples of suitable primary aminoalkoxysilanes of the formula II are 3-aminopropyltrimethoxysilane (e.g., DYNASYLAN AMMO), 3-aminopropyltriethoxysilane (e.g., DYNASYLAN AMEO), 3-aminopropylmethyldiethoxysilane (e.g., DYNASYLAN 1505), and 3-aminopropylethylene glycol oxymethoxysilane (e.g., DYNASYLAN 1302). Particular preference is given to 3-aminopropyltrimethoxysilane and 3-aminopropyltriethoxysilane.

Suitable isocyanates are aliphatic, cycloaliphatic and araliphatic, i.e., aryl-substituted aliphatic, diisocyanates and (cyclo)aliphatic diisocyanates, as described, for example, in Houben-Weyl, Methoden der organischen Chemie, volume 14/2, pages 61–70 and in the article by W. Siefken, Justus Liebigs Annalen der Chemie 562 75–136, both of which are incorporated herein by reference. Examples are 1,2-ethylene diisocyanate, 1,4-tetramethylene diisocyanate, 1,6-hexamethylene diisocyanate (HDI), 2,2,4- and 2,4,4-trimethyl-1,6-hexamethylene diisocyanate (TMDI), 1,9-diisocyanato-5-methylnonane, 1,8-diisocyanato-2,4-dimethyloctane, 1,12-dodecane diisocyanate, ω,ω'-diisocyanatodipropyl ether, cyclobutene 1,3-diisocyanate, cyclohexane 1,3- and 1,4-diisocyanate, 3-isocyanatomethyl-3,5,5-trimethylcyclohexyl isocyanate (isophorone diisocyanate (IPDI)), 1,4-diisocyanatomethyl-2,3,5,6-tetramethylcyclohexane, decahydro-8-methyl(1,4-methanonaphthyl-2-(or -3-)-5-ylenedimethylene diisocyanate, hexahydro-4,7-methanoindan-1-(or -2-)-5-(or -6-) ylenedimethylene diisocyanate, hexahydro-4,7-methanoindan-1-(or -2-)-5-(or -6-) ylene diisocyanate, 2,4- and 2,6-hexa-hydrotolylene diisocyanate, perhydro-2,4'-diphenyl-methane diisocyanate, perhydro-4,4'-diphenylmethane diisocyanate ($H_{12}$MDI), 4,4'-diisocyanato-3,3',5,5'-tetramethyldicyclohexylmethane, 4,4'-diisocyanato-2,2',3,3',5,5',6,6'-octamethyldicyclohexylmethane, (ω,ω'-diisocyanato- 1,4-diethylbenzene, 1,4-diisocyanatomethyl-2,3,5,6-tetramethylbenzene, 2-methyl-1, 5-diisocyanatopentane (MPDI), 2-ethyl-1,4-diisocyanatobutane, 1,10-diisocyantodecane, and 1,5-diisocyanatohexane. Further suitable isocyanates are described in the Annalen article cited above on page 122 f. It is generally preferred to use the following diisocyanates and their isomer mixtures, i.e., HDI, MPDI, 2,5(2,6)-bis (isocyanatomethyl)bicyclo[2.2.1]-heptane (NBDI), $H_{12}$MDI, TMDI and IPDI, with particular preference $H_{12}$MDI and IPDI, alone or in mixtures.

The free NCO content of the monoadducts of the invention is from 5 to 9% by weight. This range for the free NCO content includes all specific values and subranges therebetween, such as 6, 7 and 8% by weight. The residual fraction of monomeric diisocyanate is less than 0.6% by weight. The amount of monomeric diisocyanate in the monoadduct may be at most 0.01, 0.02, 0.05, 0.1, 0.2, 0.3, 0.4 and 0.5% by weight. The viscosity at room temperature may vary within a wide range from 200 to 20,000 mPas. This viscosity range includes all specific values and subranges therebetween, such as 500, 1,000, 2,000, 5,000, 10,000 and 15,000 mPas.

The molar ratio of diisocyanate to aminoalkylalkoxysilane depends on the permissible bisadduct (diisocyanate-aminoalkoxysilane 1:2) content. The higher the excess of diisocyanate, the smaller the amount of 1:2 adduct that will form in the course of the reaction.

The short path distillation is conducted at 80–160° C./0.04–0.2 mbar. The temperature and the subatmospheric pressure depends on guided by the viscosity behavior and thermal stability of the respective product. Especially when using diisocyanates which are not very sterically bulky, such as HDI, for example, short path destination at elevated temperatures may be accompanied by partial elimination of alcohol.

The storage stability of the monoadducts of the invention with respect to gelling and recleavage is primarily a function of the diisocyanate used. Gelling is manifested in a reduction in the NCO content and an increase in the viscosity, recleavage in an increase in the monomeric diisocyanate content. The storage stability of the monoadducts of the invention is at its best when IPDI has been used as the diisocyanate component.

The monoadducts of the invention are used as a building block for the targeted modification of polymers and also in PU coating systems and PU dispersions.

EXAMPLES

Having generally described this invention, a further understanding can be obtained by reference to certain specific examples which are provided herein for purposes of illustration only and are not intended to be limiting unless otherwise specified.

Examples 1 to 3 and Comparative Examples A–C

General Preparation Procedure

An intensively stirred mixture of from 5 to 20 mol of diisocyanate is carefully admixed dropwise with 1 mol of aminoalkylalkoxysilane such that the temperature of the reaction mixture does not exceed 100° C. The reaction is conducted under an inert gas atmosphere. After the end of the reaction, the unreacted diisocyanate is separated off by means of short path distillation at 80–160° C. and 0.04–0.2 mbar.

The monoadducts are obtained as the residue. The chemical and physical characteristics found are reproduced in Table 1.

TABLE 1

Monoadducts (1:1) of diisocyanates and secondary aminoalkylalkoxysilanes

| Example | Diisocyanate | Amino-alkyl-alkoxysilane | NCO content (theor.) [% by weight] | NCO content (found) [% by weight] | Monomer content [% by weight] |
|---|---|---|---|---|---|
| 1 | HDI | A | 6.8 | 7.0 | 0.1 |
| 2 | $H_{12}$MDI | A | 5.9 | 6.0 | 0.5 |
| 3 | IPDI | A | 6.3 | 6.4 | 0.2 |
| A | HDI | B | 11.6 | 10.0 | 1.4 |
| B | IPDI | B | 10.1 | 8.4 | 2.3 |
| C | IPDI | C | 6.5 | 5.0 | 1.5 |

A: Michael adduct of formula I of DYNASYLAN AMEO and dibutyl maleate
B: DYNASYLAN 1110 (N-methyl-3-aminopropyltrimethoxy-silane,
C: N,N-bis[(3-triethoxysilyl)propyl]amine It is found that the noninventive compounds of Comparative Examples A–C (Tab. 1) possess inadequate stability in respect of gelling and recleavage. Indicators are the high monomer contents and the NCO contents of these compounds, the latter undershooting the theoretical value by far. Storage stability studies provide a particularly clear revelation of the comparatively deficient recleavage stability of the noninventive compounds. Within a short time, the monomer contents increase dramatically to high levels (Tab. 2).

TABLE 2

Storage stability of monoadducts (1:1) of diisocyanates and secondary aminoalkylalkoxysilanes

| Example | 1:1 adduct | | Start | 4 weeks | 8 weeks | 12 weeks |
|---|---|---|---|---|---|---|
| 1 | HDI + A | NCO content [% by wt.] | 7.0 | 6.9 | 6.3 | 5.8 |
| | | Monomer [% by wt.] | 0.1 | 0.2 | 0.2 | 0.2 |
| | | Visc. at 23° C. [mPas] | 320 | 340 | 380 | 430 |
| 2 | $H_{12}$MDI + A | NCO content [% by wt.] | 6.0 | 6.1 | 6.0 | 5.8 |
| | | Monomer [% by wt.] | 0.5 | 0.5 | 0.5 | 0.4 |
| | | Visc. at 23° C. [mPas] | 7560 | 7940 | 8380 | — |
| 3 | IPDI + A | NCO content [% by wt.] | 6.4 | 6.4 | 6.2 | 6.3 |
| | | Monomer [% by wt.] | 0.2 | 0.2 | 0.2 | 0.2 |
| | | Visc. at 23° C. [mPas] | 5800 | 6100 | 6320 | 6410 |
| A | HDI + B | NCO content [% by wt.] | 10.0 | 9.9 | 9.4 | 9.3 |
| | | Monomer [% by wt.] | 1.4 | 6.3 | 7.3 | 7.7 |
| | | Visc. at 23° C. [mPas] | 290 | 400 | 510 | — |
| B | IPDI + B | NCO content [% by wt.] | 8.4 | 8.1 | 8.1 | 8.0 |
| | | Monomer [% by wt.] | 2.3 | 5.5 | 5.5 | 5.4 |
| | | Visc. at 23° C. [mPas] | 60500 | 62800 | 71300 | 74800 |

TABLE 2-continued

Storage stability of monoadducts (1:1) of diisocyanates and secondary aminoalkylalkoxysilanes

| Example | 1:1 adduct | | Start | 4 weeks | 8 weeks | 12 weeks |
|---|---|---|---|---|---|---|
| C | IPDI + C | NCO content [% by wt.] | 5.0 | 4.7 | 4.6 | 4.4 |
| | | Monomer [% by wt.] | 1.5 | 4.8 | 4.9 | 4.9 |
| | | Visc. at 23° C. [mPas] | 2500 | 2780 | 3120 | — |

A: Michael adduct of formula I of DYNASYLAN AMEO and dibutyl maleate
B: DYNASYLAN 1110 (N-methyl-3-aminopropyltrimethoxy-silane)
C: N,N-bis[(3-triethoxysilyl)propyl]amine Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 100 13 628.1, filed on Mar. 18, 2000, and incorporated herein by reference in its entirety.

What is claimed is:

1. A stable 1:1 monoadduct of
   (a) at least one aminoalkylalkoxysilane represented by formula I:

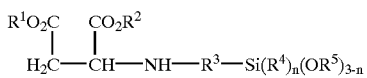
   (I)

wherein
   $R^1$ and $R^2$ are identical or different $C_1$–$C_8$ alkyl groups;
   $R^3$ is a $C_1$–$C_5$ alkylene group;
   $R^4$ and $R^5$ are identical or different $C_1$–$C_{18}$ alkyl groups or alkoxyalkyl groups having up to 5 carbon atoms; and
   n is 0, 1 or 2; and
   (b) at least one diisocyanate,
   wherein the monoadduct has a free diisocyanate content of less than 0.6% by weight.

2. The monoadduct of claim 1, wherein said at least one diisocyanate comprises at least one aliphatic, cycloaliphatic, araliphatic and/or (cyclo)aliphatic diisocyanate.

3. The monoadduct of claim 1, wherein said at least one diisocyanate comprises isophorone diisocyanate (IPDI) and/or 4,4'-methylenebis(cyclohexyl isocyanate) ($H_{12}$MDI).

4. The monoadduct of claim 1, wherein said at least one aminoalkylalkoxysilane comprises a Michael adduct of a maleic ester and 3-amino-propyltrimethoxysilane.

5. The monoadduct of claim 1, having a free diisocyanate content of at most 0.5% by weight.

6. The monoadduct of claim 1, wherein said at least one aminoalkylalkoxysilane comprises a Michael adduct of a fumaric ester and 3-amino-propyltrimethoxysilane.

7. The monoadduct of claim 1, wherein $R^1$ and $R^2$ are identical or different $C_1$–$C_4$ alkyl groups.

8. The monoadduct of claim 1, having a free diisocyanate content of at most 0.4% by weight.

9. The monoadduct of claim 1, having a free diisocyanate content of at most 0.1% by weight.

10. The monoadduct of claim 1, having a viscosity of 200 to 20,000 mPas at room temperature.

11. The monoadduct of claim 1, having a free NCO content of from 5 to 9% by weight.

12. A process for preparing the monoadduct of claim 1, comprising:
    reacting said aminoalkylalkoxysilane and said diisocyanate, to produce said monoadduct, and then
    removing unreacted diisocyanate such that the diisocyanate content of said monoadduct is less than 0.6% by weight.

13. A process for preparing the monoadduct of claim 1, comprising:
    reacting 5–20 mol of said diisocyanate with 1 mol of said aminoalkylalkoxysilane, wherein the diisocyanate is introduced initially at room temperature and the aminoalkylalkoxysilane is added dropwise to this initial charge at a rate such that the temperature increase does not exceed 100° C., and then,
    separating off the unreacted diisocyanate from the reaction product by short path distillation at 80–160° C. and 0.04–0.2 mbar.

14. A stable 1:1 monoadduct of at least one aminoalkylalkoxysilane and at least one diisocyanate having a free diisocyanate content of less than 0.6% by weight, obtained by reacting at least one secondary aminoalkylalkoxysilanes represented by formula I:

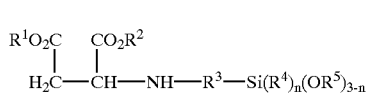
   (I)

wherein
   $R^1$ and $R^2$ are identical or different $C_1$–$C_8$ alkyl groups;
   $R^3$ is a $C_1$–$C_5$ alkylene group;
   $R^4$ and $R^5$ are identical or different $C_1$–$C_{18}$ alkyl groups or alkoxyalkyl groups having up to 5 carbon atoms; and
   n is 0, 1 or 2;
   and at least one diisocyanate, by reacting 5–20 mol of diisocyanate with 1 mol of aminoalkylalkoxysilane, the diisocyanate being introduced initially at room temperature and the aminoalkylalkoxysilane being added dropwise to this initial charge at a rate such that the temperature increase does not exceed 1000° C., and, after the end of the reaction, separating off the unreacted diisocyanate from the reaction product by means of a short path distillation at 80–1600° C. and 0.04–0.2 mbar.

* * * * *